US00PP36045P2

(12) United States Plant Patent
Lim

(10) Patent No.: US PP36,045 P2
(45) Date of Patent: Jul. 30, 2024

(54) FLORIBUNDA SHRUB ROSE PLANT NAMED 'ALTgolddragon'

(50) Latin Name: *Rosa hybrida*
Varietal Denomination: ALTgolddragon

(71) Applicant: Altman Specialty Plants Inc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,529

(22) Filed: Sep. 22, 2023

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of Rose plant named 'ALTgolddragon' is disclosed, characterized by distinctive fully double yellow flowers with a strong, lemony fragrance. Plants are vigorous and can be grown on their own roots. Plants have semi-upright, spreading habits, and flower continuously from spring to autumn. The new variety is normally produced as an outdoor garden or container plant.

1 Drawing Sheet

Latin name of the genus and species: *Rosa hybrida.*
Variety denomination: 'ALTgolddragon'.

BACKGROUND OF THE INVENTION

The new *Rosa* cultivar is a product of a planned breeding program conducted by the inventor, Peter Lim. The objective of the breeding program was to produce vigorous new garden rose varieties with continuous blooming for ornamental commercial applications. The cross resulting in this new variety was made Jun. 10, 2013.

The seed parent is unpatented variety *Rosa* 'P9505PF'. The pollen parent is the unpatented variety *Rosa* 'Westerland'. The new variety was selected in August of 2014 by the inventor in a group of seedlings resulting from the 2013 crossing, in a nursery in Vista, California.

Asexual reproduction of the new cultivar has been performed by vegetative cuttings. This was first performed at a research greenhouse in Vista, California in August of 2014 and has shown that the unique features of this cultivar are stable and reproduced true to type in more than 5 successive generations.

SUMMARY OF THE INVENTION

The cultivar 'ALTgolddragon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTgolddragon' These characteristics in combination distinguish 'ALTgolddragon' as a new and distinct *Rosa* cultivar:

1. Vigorous plant.
2. Double flower with average of 50 petals.

3. Earlier blooming.
4. Continuous flowering.
5. Plants can be grown on their own roots; grafting is not required.

PARENT COMPARIONS

Plants of the new cultivar 'ALTgolddragon' are similar to plants of the seed parent, in most horticultural characteristics, however, plants of the new cultivar 'ALTgolddragon' differ in the following:

1. Flowers of the new cultivar are yellow, while flowers of the seed parent are pink.

Plants of the new cultivar 'ALTgolddragon' are similar to plants of the pollen parent in most horticultural characteristics, however, plants of the new cultivar 'ALTgolddragon' differs in the following;

1. The new variety has a semi-upright, outwardly spreading habit, while the pollen parent has a climbing habit.

COMMERCIAL COMPARISON

Plants of the new cultivar 'ALTgolddragon' can be compared to the commercial variety *Rosa* 'KORresia', U.S. Plant Pat. No. 3,509. These varieties are similar in most horticultural characteristics, however 'ALTgolddragon' differs in the following:

1. The new variety produces about 50 petals, while this comparator produces 25 to 30 petals Plants of the new cultivar 'ALTgolddragon' can also be compared to the commercial variety *Rosa* 'WEKvossutono', U.S. Plant Pat. No. 18,473. These varieties are similar in most horticultural characteristics, however 'ALTgolddragon' differs in the following:

1. Foliage of the new variety is moderately glossy and glabrous, while the foliage of this comparator is glossy.

2. Flower color of the new variety is a lighter yellow than the flower color of this comparator.

BRIEF DESCRIPTION OF THE PHOTOGRAPH

The accompanying photograph illustrates in full color a close up of an individual flower. The plant producing this flower is approximately 18 months old; the flower is approximately 7 to 10 days old from a colored bud stage and is fully open. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTgolddragon' plants grown outdoors, in Vista, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTgolddragon'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Semi-upright, outwardly spreading.

Container size: 3-gallon.

Height: 40 cm.

Plant spread: 55 cm.

Rootstock: Own root.

Growth rate: Moderate.

Branching characteristics: Sympodial branching.

Length of primary lateral branches: Average range 12 to 22 cm.

Diameter of lateral branches: Approximately 4 to 6 mm.

Quantity of branches: 6 to 8 main branches, moderate lateral branches, 8 to 10 lateral branches per main branch.

Branches-young wood:

*Diameter.*—Approximately 4 mm.

*Texture.*—Glabrous.

*Approximate density/quantity of prickles.*—None.

*Color.*—Near RHS Yellow-Green 144C.

Branches-old wood:

*Diameter.*—Approximately 4 to 6 mm.

*Color.*—Near RHS Green 137C.

*Texture.*—Glabrous. Oldest, basal growth scaly.

*Thorns.*—

*Approximate density/quantity of thorns.*—Young growth: None. Mature growth: Sparse, irregularly occurring. Approximately 4 mm in diameter at base. 5 mm long. Colored near RHS Greyed-Orange 165C, flushed 165B.

FOLIAGE

Leaf:

*Arrangement.*—Alternate and compound.

*Quantity.*—Average 6 to 12 per main branch.

*Internode.*—Average range 2 to 3.5 cm.

*Average length.*—Approximately 10 cm.

*Average width.*—Approximately 7 cm.

Rachis:

*Average length.*—Approximately 3 cm.

*Average diameter.*—Approximately 2 mm.

*Color.*—Upper surface: Near RHS Yellow-Green 144C. Lower surface: Near RHS Yellow-Green 144D.

*Texture.*—Glabrous.

Leaflet:

*Quantity.*—5 per leaf.

*Average length.*—Approximately 4 cm.

*Average width.*—Approximately 3 cm.

*Shape of blade.*—Broad ovate.

*Apex.*—Acute.

*Base.*—Broadly rounded.

*Margin.*—Finely serrate.

*Appearance of top surface.*—Moderately glossy.

*Appearance of bottom surface.*—Matte.

*Texture of top surface.*—Glabrous.

*Texture of bottom surface.*—Glabrous.

*Color.*—Young foliage upper side: Near RHS Green 137B. Very thin Greyed-Purple 187B on margin serrations. Young foliage under side: Near RHS Green 138B. Very thin Greyed-Purple 187B on margin serrations. Mature foliage upper side: Near RHS Green 137A. Mature foliage under side: Near RHS Green 137C.

*Venation.*—Type: Reticulate. Venation color upper side: Near RHS Yellow-Green 144C. Venation color under side: Near RHS Yellow-Green 145A.

Petiole:

*Average length.*—Approximately 2.5 cm.

*Average diameter.*—Approximately 3 mm.

*Texture.*—Glabrous.

*Color.*—Upper surface: Near RHS Yellow-Green 144B. Lower surface: Near RHS Yellow-Green 144C.

*Petiole wing.*—Typically 10 mm long and 5 mm wide. Apex apiculate. Upper surface colored near RHS Yellow-Green 144B, lower surface colored near Yellow-Green 144A. Texture: Glabrous.

FLOWER

Natural flowering season: Spring until autumn.

Inflorescence type and habit: Fully double rotate flowers.

Rate of flower opening: Approximately 8 days from bud to fully opened flower.

Flower longevity on plant: About 7 days after fully opened.

Quantity of flowers: 30 to 40 fully opened flowers and buds.

Flower size:

*Diameter.*—Approximately 6 to 8.5 cm.

*Height.*—Approximately 3 to 3.5 cm.

Flower shape:

*From above.*—Round to very slightly irregular round.

*Profile of upper part of flower.*—Flat.

*Profile of lower part of flower.*—Nearly flat, lower petals reflexing slightly with age.

Peduncle:

*Length.*—2.5 cm.

*Diameter.*—3 mm.

*Color.*—Near RHS Yellow-Green 144A.

*Texture.*—Glabrous.

Petals:

*Petal arrangement.*—Multiple rotate, overlapping whorls.

*Petal quantity.*—Average 50.

*Length.*—2.5 to 3.4 cm.

*Width.*—1.3 to 2.2 cm.

*Shape.*—Obovate.

*Margin.*—Entire.

*Apex.*—Rounded with 2 to 5 irregular shallow notches.

*Base.*—Very broad attenuate.

*Texture.*—Glabrous all surfaces.

*Color.*—When opening: Upper surface: Near RHS Yellow 6A, flushed 7B. Basal spot absent. Lower surface: Near RHS Yellow 6A, flushed 7D. Fully opened: Upper surface: Near RHS Yellow 5A, flushed 6A. Basal spot absent. Lower surface: Near RHS Yellow 5B, flushed 6B. Aging: Upper surface: Near RHS Yellow 5C, flushed 4B. Basal spot absent. Lower surface: Near RHS Yellow 5D, flushed 4B.

Bud:

*Shape.*—Ovate.

*Length.*—Approximately 2.3 cm.

*Diameter.*—Approximately 1.5 cm.

*Color.*—Near RHS Yellow 2B.

Sepals:

*Quantity.*—5.

*Length.*—1.8 cm.

*Width.*—7 mm.

*Shape.*—Narrow deltoid.

*Apex.*—Apiculate. No sepal extensions.

*Margin.*—Entire.

*Texture.*—Slightly pubescent lower surface, densely and softly pubescent upper surface.

*Color.*—Interior Surface: Near RHS Green 138B, flushed 138C. Exterior Surface: Near RHS Green 137A.

Receptacle:

*Depth.*—5 mm.

*Diameter.*—8 mm.

*Shape.*—Flat.

*Color.*—Near RHS Yellow-Green 150D.

Fragrance: Strong lemony tea rose scent.

REPRODUCTIVE ORGANS

Stamens:

*Quantity.*—About 20 to 30.

*Filament length.*—Approximately 6 mm to 8 mm.

*Filament color.*—Near RHS Yellow 7C.

Anthers:

*Length.*—2 mm.

*Shape.*—Oblate.

*Color.*—Near RHS Greyed-Orange166B.

*Pollen.*—None observed.

Pistil: Misshapen 3-parted structure in center of receptacle. About 3 mm in length and 2 mm in diameter. Colored near RHS Yellow-Green 150D.

OTHER CHARACTERISTICS

Seeds and fruits: Not observed.

Disease/pest resistance: Neither resistance nor susceptibility to normal diseases and pests of roses observed.

What is claimed is:

1. A new and distinct cultivar of Rose plant named 'ALTgolddragon' as herein illustrated and described.

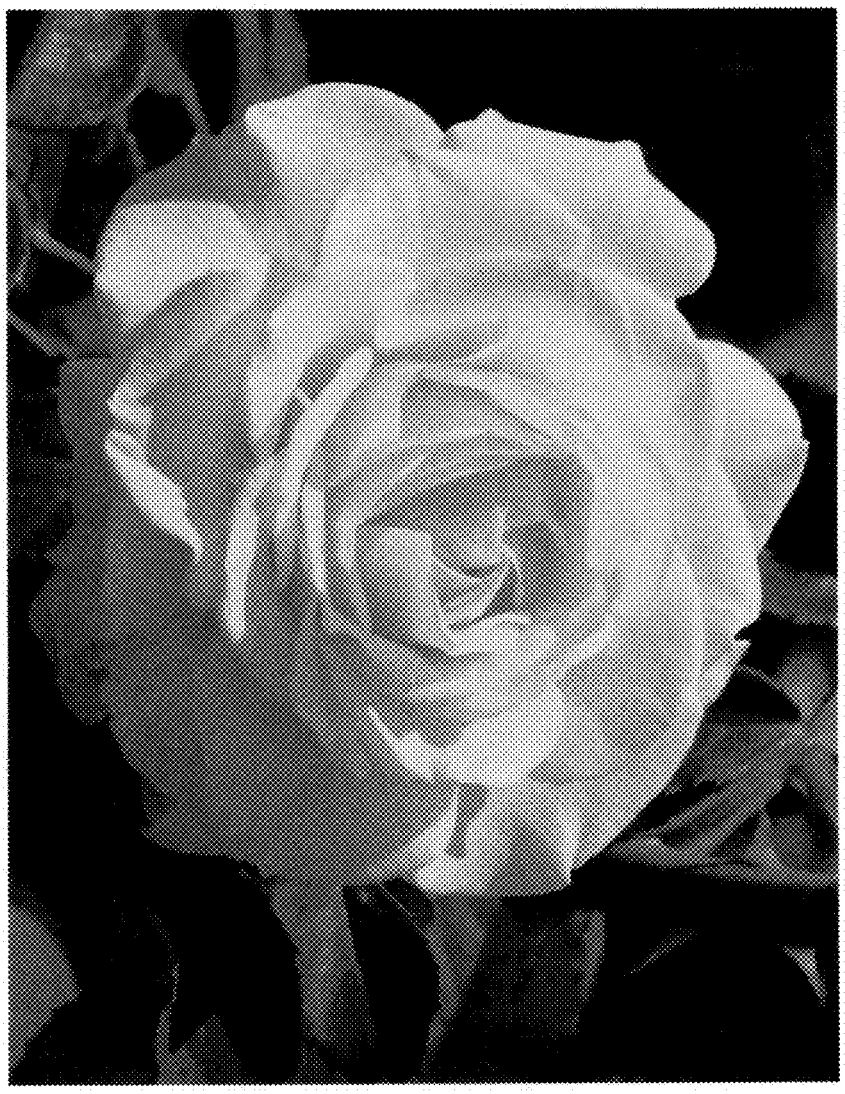

* * * * *